(12) United States Patent
Cullen et al.

(10) Patent No.: US 7,833,790 B2
(45) Date of Patent: Nov. 16, 2010

(54) WOUND DRESSINGS COMPRISING OXIDIZED CELLULOSE AND HUMAN RECOMBINANT COLLAGEN

(75) Inventors: Breda Mary Cullen, Skipton (GB); Derek Walter Silcock, Skipton (GB); Claire Boyle, Leeds (GB)

(73) Assignee: Ethicon, Inc., Somerville, NJ (US)

( * ) Notice: Subject to any disclaimer, the term of this patent is extended or adjusted under 35 U.S.C. 154(b) by 114 days.

(21) Appl. No.: 11/608,553

(22) Filed: Dec. 8, 2006

(65) Prior Publication Data

US 2007/0154530 A1 Jul. 5, 2007

(30) Foreign Application Priority Data

Dec. 9, 2005 (GB) ................... 0525130.1

(51) Int. Cl.
*A61K 38/39* (2006.01)
*A61L 15/00* (2006.01)

(52) U.S. Cl. .................... 435/445; 435/423; 514/12

(58) Field of Classification Search ................. None
See application file for complete search history.

(56) References Cited

U.S. PATENT DOCUMENTS

| 2,517,772 | A | | 8/1950 | Doub et al. |
| 3,122,479 | A | | 2/1964 | Smith |
| 5,593,859 | A | | 1/1997 | Prockop et al. |
| 5,936,035 | A | * | 8/1999 | Rhee et al. .................. 525/54.1 |
| 5,962,648 | A | | 10/1999 | Berg |
| 6,596,304 | B1 | * | 7/2003 | Bayon et al. .................. 424/444 |
| 2003/0008831 | A1 | * | 1/2003 | Yang et al. ..................... 514/21 |
| 2003/0078532 | A1 | * | 4/2003 | Ruszczak et al. .............. 602/46 |
| 2004/0241214 | A1 | * | 12/2004 | Kirkwood et al. ........... 424/445 |

FOREIGN PATENT DOCUMENTS

| EP | 0437095 A2 | 7/1991 |
| EP | 0562862 A1 | 9/1993 |
| EP | 1153622 B1 | 10/2004 |
| GB | 1280631 A | 7/1972 |
| GB | 2314842 A * | 1/1998 |
| GB | 2402882 A | 12/2004 |
| GB | 2408206 A | 5/2005 |
| WO | WO 98/00180 A1 | 1/1998 |
| WO | WO 2004/024197 A1 | 3/2004 |
| WO | WO 2004/078120 A2 | 9/2004 |

OTHER PUBLICATIONS

Veves et al., A Randomized, Controlled Trial of Promogran (a Collagen/Oxidized Regnerated cellulose Dressing) vs Standard Treatemen in the Management of Diabetic Fot Ulcers, Arch Surg, vol. 137, Jul. 2002, pp. 822-827.*

Olsen, D. et al., *Recombinant Collagen and Gelatin for Drug Delivery*, Advanced Drug Delivery Reviews, 55, 2003, pp. 1547-1567.

* cited by examiner

*Primary Examiner*—Lisa J Hobbs

(57) ABSTRACT

A wound dressing composition comprising a human recombinant collagen and an oxidized cellulose. For example, the composition may be in the form of a sponge formed by freeze drying an aqueous dispersion of human recombinant collagen and oxidized regenerated cellulose (ORC). The composition is especially suitable for the treatment of chronic wounds.

12 Claims, No Drawings

WOUND DRESSINGS COMPRISING OXIDIZED CELLULOSE AND HUMAN RECOMBINANT COLLAGEN

CROSS-REFERENCE TO RELATED APPLICATION

This application claims the benefit of GB 0525130.1 filed on Dec. 9, 2005. All documents cited herein are incorporated by reference in their entirety.

FIELD OF THE INVENTION

The present invention relates to wound dressing compositions comprising an oxidized cellulose and a human recombinant collagen, and the uses thereof for wound healing.

BACKGROUND OF THE INVENTION

Oxidized cellulose is produced by the oxidation of cellulose, for example with dinitrogen tetroxide. This process converts primary alcohol groups on the saccharide residues to carboxylic acid group, forming uronic acid residues within the cellulose chain. The oxidation does not proceed with complete selectivity, and as a result hydroxyl groups on carbons 2 and 3 are occasionally converted to the keto form. These ketone units introduce an alkali labile link, which at pH 7 or higher initiates the decomposition of the polymer via formation of a lactone and sugar ring cleavage. As a result, oxidized cellulose is biodegradable and bioabsorbable under physiological conditions.

The preferred oxidized cellulose for practical applications is oxidized regenerated cellulose (ORC) prepared by oxidation of a regenerated cellulose, such as rayon. It has been known for some time that ORC has haemostatic properties. ORC has been available as a haemostatic product called SURGICEL (Registered Trade Mark of Johnson & Johnson Corporation) since 1950. This product is produced by the oxidation of a knitted rayon material.

A modification of porosity, density and knit pattern led to the launch of a second ORC fabric product, INTERCEED (Registered Trade Mark-Johnson & Johnson Corporation) which was shown to reduce the extend of post-surgical adhesions in abdominal surgery.

U.S. Pat. No. 2,517,772 (Doub et al.) describes improved haemostatic materials obtained by impregnating ORC fabric with thrombin.

EP-A-0437095 describes a neutralised ORC material prepared by contacting an as-synthesised acidic ORC material with a solution of a basic salt of a weak organic acid, such as sodium acetate. The resulting neutralised product is indicated for haemostasis and adhesion prevention.

EP-A-0562862 describes bioabsorbable sponge materials for use as wound implants. The materials comprise a collagen sponge matrix having an oriented substructure therein. The matrix and/or substructures may comprise oxidized regenerated cellulose. There is no disclosure of the use of such materials for the treatment of chronic wounds.

WO98/00180 describes the use of freeze-dried sponges of collagen admixed with oxidized regenerated cellulose (ORC) for the treatment of chronic wounds. EP-A-1153622 further describes sterile sponge pads of this type based on bovine collagen/ORC mixtures that exhibit high reproducibility and tensile strength both when wet and when dry. The sponge pad described in EP-A-1153622 is freeze-dried and at least 80% by weight of the sponge consists of a mixture of bovine collagen and oxidized regenerated cellulose in the weight ratio 60:40 to 40:60.

Sponges of bovine collagen mixed with ORC made in accordance with EP-A-1153622 are commercially available from Ethicon, Inc. under the Registered Trade Mark PROMOGRAN. These products have been highly successful, especially for the treatment of chronic wounds. The materials are of natural, biological origin (albeit chemically modified), and consequently tend to have low antigenicity. The materials are generally bioabsorbable, which reduces the trauma associated with removal of conventional wound dressing materials from the surface of the wound. Furthermore, some of these materials can have positive therapeutic effects on wound healing.

It is an object of the present invention to provide improved wound dressing materials for mammalian wounds, and especially for human, chronic wounds, such as venous ulcers, decubitis ulcers and diabetic ulcers. Such chronic wounds generally exhibit little or no bleeding or adhesion to other body tissues.

SUMMARY OF THE INVENTION

The present invention is directed to a wound dressing composition comprising a human recombinant collagen and an oxidized cellulose.

DETAILED DESCRIPTION OF THE INVENTION

Accordingly, in a first aspect the present invention provides a wound dressing composition comprising a human recombinant collagen and an oxidized cellulose. It has surprisingly been found that the use of human recombinant collagen instead of bovine collagen in a freeze-dried sponge causes human dermal fibroblasts to proliferate to a greater extent than when a freeze-dried sponge comprising bovine collagen is used.

Preferably, the oxidized cellulose comprises oxidized regenerated cellulose (ORC). The oxidized regenerated cellulose (ORC) can be obtained by the process described in U.S. Pat. No. 3,122,479, the entire content of which is incorporated herein by reference. This material offers numerous advantages including the features that it is biocompatible, biodegradable, non-immunogenic and readily commercially available. ORC is available with varying degrees of oxidation and hence rates of degradation. The ORC may be used in the form of insoluble fibers, including woven, non-woven and knitted fabrics. In other embodiments, the ORC is in the form of water-soluble low molecular weight fragments obtained by alkali hydrolysis of ORC.

In preferred embodiments, the oxidized cellulose is in the form of particles, such as fiber particles or powder particles, preferably dispersed in a suitable solid or semisolid topical medicament vehicle. In particular, the materials preferably contain ORC fibers, wherein a volume fraction of at least 80% of the fibers have lengths in the range of 20 μm to 1000 μm. Such a size distribution can be achieved, for example, by milling an ORC cloth, followed by sieving the milled powder to remove fibers outside the range. Preferably, the average (mean by volume) length of the ORC fibers is in the range 250 μm to 450 μm. The selection of ORC fiber lengths in this range results in easy mixing of the ORC and human recombinant collagen and highly homogeneous products. The ORC is more thoroughly complexed with the human recombinant collagen, which results in enhanced therapeutic properties of the sponge.

Preferably, the oxidised cellulose has an average molecular weight greater than 50,000. Such oxidised cellulose is substantially insoluble in wound fluids, but will undergo very gradual breakdown into bioresorbable fragments at physiological pH. Preferably, the oxidized cellulose is not neutralized. However, the present invention encompasses the use of partially or completely neutralised materials as described in EP-A-0437095 for the preparation of medicaments for the treatment of chronic wounds as hereinbefore defined.

The term "human recombinant collagen" refers to collagen manufactured by culturing a non-human organism to express at least one human gene encoding a collagen. The human recombinant collagen is suitably selected from the group consisting of collagen type I, type II, type III, type IV, type V, type VI, type VII, type VIII, type IX, type X, type XI, type XII, type XIII, type XIV, type XV, type XVI, type XVII, type XVIII, type XIX, type XX, type XXI, type XXII, type XXIII, type XXIV, type XXV, type XXVI, and type XXVII. The collagen can be collagen of one type free of any other type, or can be a mixture of collagen types. Suitably, the collagen comprises, or consists essentially of, collagens selected from the group consisting of type I collagen, type III collagen, and mixtures thereof.

Human recombinant collagen may be provided by any suitable method known in the art. For example, the step of providing human recombinant collagen may comprise following the protocol described in U.S. Pat. No. 5,962,648, the entire content of which is incorporated herein by reference. Further recombinant processes are set forth in U.S. Pat. No. 5,593,859 and WO2004/078120, which are also incorporated herein by reference. Preferably, collagen will be recombinantly manufactured by culturing a cell which has been transfected with at least one gene encoding the polypeptide comprising collagen and genes encoding the oc and subunits of the post-translational enzyme prolyl 4-hydroxylase and purifying the resultant collagen monomer therefrom. The recombinant collagen solution may be subsequently subjected to polymerization or cross-linking conditions to produce an insoluble fibrous collagen.

Bovine collagen is a mixture of collagen type I (85%) and collagen type III (15%), a combination which is set by nature and cannot be varied. An advantage of recombinant collagen is that collagen type I and collagen type III are made independently of one another, and so any combination of type I and type III collagen can be made. The products according to the present invention may suitably comprise human collagen type I and human collagen type III in any ratio. For example, the products may comprise human collagen type I and human collagen type III in a ratio by weight of 100:0, 80:20, 60:40, 50:50, 40:60, 20:80 or 0:100, or anywhere in-between. Preferably, the ratio by weight of human collagen type I:human collagen type III is greater than about 50:50, and preferably it is greater than about 70:30, for example about 80:20. Suitably, the type I human recombinant collagen makes up at least about 75% by weight of the total human recombinant collagens in the material.

The compositions according to the present invention preferably comprise an intimate mixture of the human recombinant collagen and the oxidized cellulose. Preferably, the intimate mixture comprises a mixed solution or dispersion of the human recombinant collagen and the oxidized cellulose in a suitable vehicle, such as a solvent, or a solid composition produced by removing solvent from such a solution or dispersion. (By dispersion is meant a distribution of discrete solid particles in the vehicle, e.g., a colloidal dispersion or dispersion formed by shear mixing). Such intimate mixing results in maximum chemical complexation between the amine groups of the human recombinant collagen and the carboxylate groups on the oxidized cellulose. All percentages and ratios herein are weight percentages and ratios.

Preferably, the human recombinant collagen makes up at least 5%, more preferably at least 10%, 20% or 30% by weight of the composition. Preferably, the oxidized cellulose also makes up at least 5%, more preferably at least 10%, 20% or 30% by weight of the composition. Preferably, the human recombinant collagen and oxidized cellulose together make up at least 25% by weight, more preferably 50% or 75% by weight of the wound dressing material, and in some embodiments at least 90% by weight of the material. In certain preferred embodiments, the material consists essentially of the human recombinant collagen and oxidized cellulose.

Other components of the material according to the invention may include 0-25% by weight, for example from about 1 to about 20% by weight, of one or more other biocompatible polysaccharides, for example alginates such as sodium alginate or calcium alginate, starch derivatives such as sodium starch glycolate, cellulose derivatives such as methyl cellulose or carboxymethyl cellulose, or glycosaminoglycans such as hyaluronic acid or its salts, chondroitin sulfate or heparan sulfate. The materials according to the present invention may also comprise up to about 25% by weight, for example from about 1 to about 20% by weight, of one or more additional structural proteins selected from the group consisting of fibronectin, fibrin, laminin, elastin, collagens other than human recombinant collagen, and mixtures thereof.

The materials according to the present invention may also comprise up to about 20% by weight, preferably from about 2% to about 10% by weight of water. The material according to the present invention may also contain 0-40% by weight, for example from about 5 to about 25% by weight, of a plasticiser, preferably a polyhydric alcohol such as glycerol or sorbitol.

In certain embodiments, the materials according to the present invention may also comprise up to about 10% by weight, for example from about 0.01 to about 5% by weight, typically from about 0.1 to about 2% by weight of one or more therapeutic wound healing agents, such as non-steroidal anti-inflammatory drugs (e.g. acetaminophen), steroids, local anaesthetics, antimicrobial agents, or growth factors (e.g. fibroblast growth factor or platelet derived growth factor). The antimicrobial agent may, for example, comprise an antiseptic, an antibiotic, or mixtures thereof. Preferred antibiotics include tetracycline, penicillins, terramycins, erythromycin, bacitracin, neomycin, polymycin B, mupirocin, clindamycin and mixtures thereof. Preferred antiseptics include silver, including colloidal silver, silver salts including salts of one or more of the anionic polymers making up the material, silver sulfadiazine, chlorhexidine, povidone iodine, triclosan, sucralfate, quaternary ammonium salts and mixtures thereof. These medicated wound dressing materials according to the invention provide sustained release of the therapeutic agents as the wound dressing material breaks down in use.

All of the above percentages are on a dry weight basis.

Preferably, the weight ratio of human recombinant collagen to oxidized cellulose is from about 1:99 to about 99:1. More preferably, the weight ratio is in the range about 1:9 to about 9:1, more preferably it is in the range about 4:1 to about 1:4, still more preferably in the range about 2:1 to about 1:2, and most preferably in the ratio human recombinant collagen: oxidized cellulose of from about 60:40 to about 50:50. In certain embodiments the material consists essentially of about 55 wt % human recombinant collagen and about 45 wt % oxidized cellulose, on a dry weight basis.

The composition according to the present invention may be in any convenient form, such as a powder, microspheres, flakes, a mat or a film.

In certain embodiments, the composition according to the present invention is in the form of a semisolid or gel ointment for topical application.

In certain embodiments, the composition according to the present invention is in the form of a freeze-dried or solvent-dried bioabsorbable sponge for application to a chronic wound. Preferably, the average pore size of the sponge is in the region of 10-500 μm, more preferably about 100-300 μm. A suitable sponge has been made by freeze-drying or solvent drying an aqueous dispersion consisting essentially of human recombinant collagen particles or fibers and ORC fibers, together with suitable therapeutic agents.

Suitably, the materials according to the present invention are freeze-dried sponges of human recombinant collagen and ORC substantially as described in EP-A-1153622, the entire content of which is incorporated herein by reference.

In yet other embodiments, the composition according to the present invention is in the form of a flexible film, which may be continuous or interrupted (e.g. perforated). The flexible film preferably comprises a plasticiser to render it flexible, such as glycerol.

In a second aspect the present invention provides a wound dressing comprising a wound dressing composition according to the first aspect of the invention. The wound dressing may consist essentially of the wound dressing material according to the invention, for example it may consist of a sheet of the material, in which case the dressing would normally be used in conjunction with a suitable secondary dressing.

The wound dressing is preferably in sheet form and comprises an active layer of the composition according to the invention. The active layer would normally be the wound contacting layer in use, but in some embodiments it could be separated from the wound by a liquid-permeable top sheet. Preferably, the area of the active layer is from about 1 cm$^2$ to about 400 cm$^2$, more preferably from about 4 cm$^2$ to about 100 cm$^2$.

Preferably, the article further comprises a backing sheet extending over the active layer opposite to the wound facing side of the active layer. Preferably, the backing sheet is larger than the active layer such that a marginal region of width 1 mm to 50 mm, preferably 5 mm to 20 mm extends around the active layer to form a so-called island dressing. In such cases, the backing sheet is preferably coated with a pressure sensitive medical grade adhesive in at least its marginal region.

Preferably, the backing sheet is substantially liquid-impermeable. The backing sheet is preferably semipermeable. That is to say, the backing sheet is preferably permeable to water vapour, but not permeable to liquid water or wound exudate. Preferably, the backing sheet is also microorganism-impermeable.

Suitable polymers for forming the backing sheet include polyurethanes and poly alkoxyalkyl acrylates and methacrylates such as those disclosed in GB-A-1280631. Preferably, the backing sheet comprises a continuous layer of a high density blocked polyurethane foam that is predominantly closed-cell. A suitable backing sheet material is the polyurethane film available under the Registered Trade Mark ESTANE 5714F.

The adhesive layer (where present) should be moisture vapor transmitting and/or patterned to allow passage of water vapor therethrough. The adhesive layer is preferably a continuous moisture vapor transmitting, pressure-sensitive adhesive layer of the type conventionally used for island-type wound dressings. Polyurethane-based pressure sensitive adhesives are preferred.

The dressing may further comprise an absorbent layer between the active layer and the protective sheet, especially if the dressing is for use on exuding wounds. The optional absorbent layer may be any of the layers conventionally used for absorbing wound fluids, serum or blood in the wound healing art, including gauzes, nonwoven fabrics, superabsorbents, hydrogels and mixtures thereof. Suitably, the absorbent layer or layers are substantially coextensive with the human recombinant collagen/ORC layer.

The wound facing surface of the dressing may be protected by a removable cover sheet. The cover sheet is normally formed from flexible thermoplastic material. Suitable materials include polyesters and polyolefins. Preferably, the adhesive-facing surface of the cover sheet is a release surface. That is to say, a surface that is only weakly adherent to the active layer and the adhesive on the backing sheet to assist removal of the cover sheet. For example, the cover sheet may be formed from a non-adherent plastic such as a fluoropolymer, or it may be provided with a release coating such as a silicone or fluoropolymer release coating.

Preferably, the wound dressing of the present invention is sterile and packaged in a microorganism-impermeable container.

In a further aspect, the present invention provides the use of a wound dressing composition according to the first aspect of the invention for the preparation of a dressing for the treatment of a wound. Preferably, the wound is a chronic wound, for example a wound selected from the group consisting of venous ulcers, decubitis ulcers and diabetic ulcers.

In a further aspect, the present invention provides a method of causing fibroblasts to proliferate comprising contacting the fibroblasts with a wound dressing material of the invention. Preferably, the fibroblasts are dermal fibroblasts. More preferably, the fibroblasts are human. The method may be carried out in vivo or in vitro. Preferably the method achieves greater fibroblast proliferation than that achieved with a wound dressing material of the same type made with bovine collagen. Suitably, the increase in fibroblast proliferation measured as described hereinafter is greater than about 40%, and preferably it is more than about 50% of the difference between the negative and positive controls.

In a further aspect, the present invention provides a method of inactivating matrix metalloproteinases (MMPs) comprising contacting the matrix metalloproteinases with a wound dressing material of the invention. The method may be carried out in vivo or in vitro.

In a further aspect, the present invention provides a method of treatment of a chronic wound in a mammal, such as a decubitis ulcer, a venous ulcer or a diabetic ulcer. The method comprises applying a wound dressing material according to the invention to the wound.

Preferably, the dressing is applied to the chronic wound for a period of at least 1 hour, more preferably at least 6 hours, and most preferably at least 12 hours. The treatment may be extended for several days or weeks, with dressing changes as appropriate, if necessary for chronic wounds. This contrasts with haemostatic applications of ORC, which typically last only a few seconds or minutes.

Without wishing to the bound by any theory, it is thought that the human recombinant collagen/oxidized cellulose compositions promote chronic wound healing in at least some of the following ways. Firstly, the complex binds to growth factors such as PDGF, EGF and FGF to retain these growth factors at the wound site. Otherwise, such growth factors tend to be carried away from the wound site along with the wound exudate. The gradual breakdown of human recombinant collagen/oxidized cellulose at physiological pH results in gradual release of the growth factors back into the wound. A second reason is that the material is fully bioresorbable and physiologically acceptable. A further reason is that the materials promote dermal fibroblast proliferation. A further reason is that the materials inactivate certain host-derived protease enzymes (matrix metalloproteinases) that are present at elevated levels in chronic wound fluid, and that contribute to poor wound healing.

The human recombinant collagen/oxidized cellulose complexes used in the present invention can be made by a process comprising the steps of: providing an dispersion of a human recombinant collagen in a suitable solvent, preferably an aqueous dispersion; immersing or dispersing oxidized cellulose in the solvent; followed by removing solvent from the dispersion to leave a solid material comprising human recombinant collagen complexed with oxidized cellulose.

The oxidized cellulose may be added to the aqueous dispersion of human recombinant collagen in the form of a suspension or solution of the oxidized cellulose, preferably at a comparable pH to the human recombinant collagen suspension, following by mixing by stirring or homogenisation. Alternatively, dry fibers or fabric of oxidized cellulose may be dispersed or immersed in the aqueous dispersion of human recombinant collagen.

The optional, additional components in the materials according to the present invention are preferably included in the dispersion prior to removal of solvent from the dispersion.

Preferably, the pH of the dispersion is adjusted in the range of about 1 to about 10, preferably pH about 2 to about 8. Oxidized cellulose undergoes hydrolysis to soluble fragments at high pH.

The solvent can be removed from the dispersion by evaporation, for example by evaporation from the dispersion in a tray to leave a film of material. In other embodiments the solvent, preferably water, is removed by freeze-drying (lyophilizing) or solvent-drying to produce the material in the form of a sponge. Preferably, the solvent dispersion contains 5-30 mg/ml of human recombinant collagen.

In certain embodiments the process may further comprise treating the human recombinant collagen and/or the oxidized cellulose in the dispersion, or in the dried material, with a cross-linking agent such as epichlorhydrin, carbodiimide, hexamethylene diisocyanate (HMDI) or glutaraldehyde.

Alternatively, cross-linking may be carried out dehydrothermally. The method of cross-linking can markedly affect the final product. For example, HMDI cross-links the primary amino groups on the human recombinant collagen within the complex, whereas carbodiimide cross-links carbohydrate on the ORC to primary amino groups on the human recombinant collagen.

It will be appreciated that any additional or alternative features that are described above in relation to any one aspect of the invention are also alternative or additional features in relation to any other aspect of the invention, either alone or in combination.

Specific embodiments of the present invention will now be described further, by way of example.

REFERENCE EXAMPLE 1

Preparation of a Bovine Collagen/fibrous ORC Sponge

A freeze-dried collagen/ORC sponge is prepared as follows.

First, the collagen component is prepared from bovine corium as follows. Bovine corium is split from cow hide, scraped and soaked in sodium hypochlorite solution (0.03% w/v) to inhibit microbial activity pending further processing. The corium is then washed with water and treated with a solution containing sodium hydroxide (0.2% w/v) and hydrogen peroxide (0.02% w/v) to swell and sterilize the corium at ambient temperature. The corium splits then undergo an alkali treatment step in a solution containing sodium hydroxide, calcium hydroxide and sodium bicarbonate (0.4% w/v, 0.6% w/v and 0.05% w.v, respectively) at pH greater than 12.2, ambient temperature, and for a time of 10-14 days, with tumbling, until an amide nitrogen level less than 0.24 mmol/g is reached. The corium splits then undergo an acid treatment step with 1% hydrochloric acid at ambient temperature and pH 0.8-1.2. The treatment is continued with tumbling until the corium splits have absorbed sufficient acid to reach a pH less than 2.5. The splits are then washed with water until the pH value of corium splits reaches 3.0-3.4. The corium splits are then comminuted with ice in a bowl chopper first with a coarse comminution and then with a fine comminution setting. The resulting paste, which is made up in a ratio of 650 g of the corium splits to 100 g of water, as ice, is frozen and stored before use in the next stage of the process. However, the collagen is not freeze-dried before admixture with the ORC in the next stage.

The ORC component of the freeze-dried pad is prepared as follows. A SURGICEL cloth (Johnson & Johnson Medical, Arlington) is milled using a rotary knife cutter through a screen-plate, maintaining the temperature below 60° C.

The milled ORC powder and the required weight (according to solids content) of frozen collagen paste are then added to a sufficient amount of water acidified with acetic acid to obtain a pH value of 3.0 and a total solids content of 1.0%. The mixture is homogenized through a Fryma MZ130D homogenizer, progressively diminishing the settings to form a homogeneous slurry. The pH of the slurry is maintained at 2.9-3.1. The slurry temperature is maintained below 20° C., and the solids content is maintained at 1%±0.07.

The resulting slurry is pumped to a degassing vessel. Vacuum is initiated for a minimum of 30 minutes, with intermittent stirring, to degas the slurry. The slurry is then pumped into freeze-drier trays to a depth of 25 mm. The trays are placed onto freezer shelves where the temperature has been preset to −40° C. The freeze-drier programme is then initiated to dry and dehydrothermally cross-link the collagen and ORC to form thick sponge pads. On completion of the cycle, the vacuum is released, the freeze-dried blocks are removed, and are then split to remove the top and bottom surface layers, and to divide the remainder of the blocks into 3 mm-thick pads. The step of splitting the freeze-dried blocks into pads is carried out with a Fecken Kirfel K1 slitter. Finally, the pads are die-cut to the desired size and shape on a die-cutter, packaged, and sterilized with 18-29 KGy of cobalt 60 gamma-irradiation. Surprisingly, this irradiation does not cause significant denaturation of the collagen, which appears to be stabilized by the presence of ORC. The resulting freeze-dried collagen ORC pads have a uniform, white, velvety appearance. The thickness of the pads is 3.2±0.17 mm (N=8 batches). These pads are used as the positive control in the Procedures described below.

EXAMPLE 1

Preparation of a Human Recombinant Collagen/fibrous ORC Sponge

Human recombinant collagen/fibrous ORC sponges were prepared as described in Reference Example 1, but with replacement of the collagen by an equal weight fraction of human recombinant collagen. The human recombinant collagen was obtained from Fibrogen Inc., 225 Gateway Boulevard, South San Francisco, Calif., 94080. The collagen was produced from genetically modified yeast and crosslinked to achieve a consistency comparable to that of the bovine material. The human recombinant collagen was equal to the bovine collagen in its susceptibility to trypsin digestion. A number of different sponges with varying ratios of type I : type III human recombinant collagen were made.

Procedure 1: Human Dermal Fibroblast Proliferation Assay

The human dermal fibroblast proliferation assay was carried out as follows.

Prototype extracts were prepared as follows—1 mg of each wound dressing material to be tested was placed in 1 ml of serum free medium and incubated for 24 hours at 37° C. under sterile conditions.

Adult human dermal fibroblasts were grown and maintained in DMEM 10% FBS (standard culture medium; Dulbecco's miminal essential medium; foetal bovine serum). These cells were routinely subcultured and used for experimental testing when 95% confluent. Adult human dermal fibroblasts were harvested at 95% confluency and re-seeded in a 96-well microtitre plate (100 ml/well) in DMEM+10% FBS at a cell density of 2.5×104 cells/ml. Cells were allowed to adhere to the plate surface for 24 hours in a humidified incubator at 37° C., 5% $CO_2$. The medium was then removed by aspiration and the cell monolayer washed with serum-free DMEM.

The test samples (extracts of each prototype) were then added to the cell monolayer (100 ml/well). Six replicates of each test sample were measured. All samples were incubated with the cells for 48 hours at 37° C., 5% $CO_2$. After this incubation period the conditioned medium was removed by aspiration and replaced with a labelling solution from a commercial cell proliferation kit (XTT, Cell Proliferation kit II, Cat. No. 1 465 015, obtained from Boehringer Mannheim). Once this solution was added an initial absorbance reading was obtained at 450 nm, after which the microtitre plate was incubated at 37° C., 5% $CO_2$ and the absorbance monitored over 4 hours. Absorbance measurements were carried out on a Thermolabsystems Multiskan Spectrum apparatus.

The proliferative effect of each prototype was evaluated by comparing the absorbance readings measured against positive and negative controls. Serum-containing growth medium (10% FBS in DMEM) was used as a positive control, and serum-free medium was used as a negative control. The results are shown in Table 1. The measured effect on human dermal fibroblast growth is represented as a percentage of the increase in cell proliferation between the negative control (at 0%) and the positive control (at 100%).

Procedure 2: Matrix Metalloproteinase Inhibition

Frozen samples of wound fluid from six different patients were defrosted and diluted as appropriate.

Wound dressing samples were 6 mm diameter biopsy punch samples taken from the freeze-dried sheet materials. In the following test procedures, a sample of the collagen/ORC sponge prepared as described in Reference Example 1 was used as a positive control. A sample of SOF-WICK (Registered Trade Mark) gauze was used as a negative control.

The dressing samples were pre-soaked for a few seconds in phosphate buffered saline (PBS), the excess being removed by slight pressure before adding the dressing samples to respective samples of the wound fluids. The wound fluids were incubated with the dressing samples at 37° C. Samples of the incubated wound fluids were taken at time points T=30 minutes and T=60 minutes.

The activity levels of matrix metalloproteinases present in the wound fluid samples were measured spectrofluorimetrically using substrate activity assays. The substrates comprise short peptides synthesised to mimic the appropriate enzyme cleavage site and contain a fluorescent reporter group, which is released upon hydrolysis. Enzyme activity was determined by measuring the rate of production of the fluorimetric compound, 7-amino 4-methyl coumarin. Activity was expressed either as relative fluorescence units per minute (RFU/min). Each sample was tested times 6 and the average value calculated. The substrate was prepared at a 10 mM-stock concentration, and diluted to a working concentration of 0.5 mM in the appropriate assay buffer. The reaction mixture, combined in a microtiter well (black, flat bottomed) comprised 5 μl wound fluid, 175 μl assay buffer and 20 μl substrate (final concentration 50 μM). The microtiter plate was read immediately at 455 nm (excitation 383 nm) and at timed intervals over the next hour; between readings the plate was covered and incubated at 37° C. Matrix metalloproteinase-like activity was estimated utilising the substrate Succinyl-Glycine-Proline-Leucine-Glycine-Proline 7-amino 4-methyl coumarin (Bachem, UK, Ltd.) solubilised in methanol. The assay buffer necessary for maximal MMP activity was 40 mM Tris/HCl, pH 7.4 containing 200 mM NaCl and 10 mM $CaCl_2$. Fluorescence measurements were carried out on a Dynex Technologies Fluorolite 1000 apparatus.

The results are shown in Table 2 (for T=30 minutes) and Table 3 (for T=60 minutes). The tables show measured MMP

TABLE 1

| Sample | 100% Type I 0% Type III | 0% Type 100% Type III | 80% Type I 20% Type III | 60% Type I 40% Type III | 40% Type I 60% Type III | 20% Type I 80% Type III | Reference Example 1 |
|---|---|---|---|---|---|---|---|
| Mean | 91.4 | 55.1 | 71.4 | 77.8 | 74.7 | 64.0 | 20 |
| Std. dev | 13.7 | 16.5 | 8.8 | 14.4 | 20.5 | 26.1 | 5.4 |

Thus, it can be seen that Reference Example 1 exhibits a small increase in fibroblast proliferation over the negative control, but the increase is only 20% of the increase that is achieved by the positive control. In contrast, the compositions according to the invention achieve from 55.1% to 91.4% of the increase in fibroblast proliferation achieved by the positive control.

The cell proliferation data presented in Table 1 show that all of the human recombinant formulations out-performed the bovine collagen equivalent of Reference Example 1.

activities in RFU/min for the six wound fluid samples (rows 1 to 6 of the tables, respectively), mean values in RFU/min (row 7), and percentage MMP activity remaining (row 8).

Only small variations were observed in MMP inhibition for the different formulations according to the invention. However, the 80:20 formulation of human type I:III was better than the others. The inhibition of the MMPs by the materials according to the invention was apparently slightly less than the inhibition obtained for the material of Reference Example 1 (which comprises bovine collagen), but the difference is not considered to be significant.

TABLE 2

| 100% Type III 0% Type I | 80% Type III 20% Type I | 60% Type III 40% Type I | 40% Type III 60% Type I | 20% Type III 80% Type I | 0% Type III 100% Type I | Reference Example 1 | Control |
|---|---|---|---|---|---|---|---|
| 0.542 | 0.835 | 0.56 | 0.626 | 0.141 | 0.52 | 0.182 | 1.624 |
| 1.036 | 0.735 | 0.723 | 0.683 | 0.452 | 0.674 | 0.266 | 1.824 |
| 0.553 | 0.824 | 0.664 | 0.723 | 0.334 | 0.615 | 0.222 | 1.817 |
| 0.501 | 0.655 | 0.8 | 0.599 | 0.495 | 0.577 | 0.409 | 1.777 |
| 0.786 | 0.824 | 0.664 | 0.723 | 0.334 | 0.615 | 0.222 | 1.817 |
| 0.591 RFU/min | 0.687 | 0.615 | 0.626 | 0.581 | 0.607 | 0.252 | 1.81 |
| 0.668 % | 0.760 | 0.671 | 0.663 | 0.390 | 0.601 | 0.259 | 1.778 |
| 37.6 | 42.7 | 37.7 | 37.3 | 21.9 | 33.8 | 14.6 | 100.0 |

TABLE 3

| 100% Type III 0% Type I | 80% Type III 20% Type I | 60% Type III 40% Type I | 40% Type III 60% Type I | 20% Type III 80% Type I | 0% Type III 100% Type I | Reference Example 1 | Control |
|---|---|---|---|---|---|---|---|
| 0.087 | 0.38 | 0.233 | 0.047 | 0 | 0.127 | 0 | 0.733 |
|  | 0.36 | 0.18 | 0.04 | 0 | 0.213 | 0.007 | 1.367 |
| 0.033 | 0.007 | 0.193 | 0.193 | 0 | 0.153 | 0 | 1.4 |
| 0.06 | 0 | 0.28 | 0.347 | 0.027 | 0.34 | 0 | 1.553 |
| 0.207 | 0.38 | 0.147 | 0.313 | 0.333 | 0.173 | 0.04 | 1.42 |
| 0.067 RFU/min | 0.4 | 0.033 | 0.28 | 0.047 | 0.233 | 0 | 1.033 |
| 0.096 % | 0.255 | 0.178 | 0.203 | 0.068 | 0.207 | 0.008 | 1.251 |
| 7.6 | 20.3 | 14.2 | 16.3 | 5.4 | 16.5 | 0.6 | 100.0 |

The above examples are intended for the purpose of illustration only. Many other embodiments falling within the scope of the accompanying claims will be apparent to the skilled reader.

What is claimed is:

1. A wound dressing composition comprising a human recombinant collagen and an oxidized cellulose, wherein the human recombinant collagen is selected from type I human recombinant collagen and type III human recombinant collagen mixtures and wherein the ratio by weight of type I human recombinant collagen to type III human recombinant collagen is greater than 70:30.

2. The wound dressing composition according to claim 1, wherein the human recombinant collagen and the oxidized cellulose are mixed in the wound dressing composition.

3. The wound dressing composition according to claim 1, wherein said oxidized cellulose is in the form of dispersed fibers or powder.

4. The wound dressing composition according to claim 3, wherein the oxidized cellulose comprises oxidized regenerated cellulose (ORC).

5. The wound dressing composition according to claim 1, comprising human recombinant collagen type I and human recombinant collagen type III in the ratio about 80:20.

6. The wound dressing composition according to claim 1 or 5, wherein the oxidized cellulose and the human recombinant collagen together make up at least 25% by weight of the material on a dry weight basis.

7. The wound dressing composition according to claim 1 or 5, wherein the oxidized cellulose and the human recombinant collagen together make up at least 50% by weight of the material on a dry weight basis.

8. The wound dressing composition according to claim 4, wherein the composition further comprises from about 0.01 to about 5% by weight on a dry weight basis of one or more wound healing therapeutic substances.

9. The wound dressing composition according to claim 4, wherein the weight ratio of human recombinant collagen to oxidized cellulose is from 1:10 to 10:1.

10. The wound dressing composition according to claim 9, wherein the weight ratio of human recombinant collagen to oxidized cellulose is in the range 1:4 to 4:1.

11. A wound dressing comprising a wound dressing composition according to claim 1 or 5.

12. A wound dressing package comprised of:
   (a) a microorganism impermeable container; and
   (b) the wound dressing according to claim 11 packaged therein, wherein the wound dressing is sterile.

* * * * *